US 6,733,789 B1

United States Patent
Stark et al.

(10) Patent No.: US 6,733,789 B1
(45) Date of Patent: May 11, 2004

(54) MULTIPARTICULATE BISOPROLOL FORMULATION

(75) Inventors: Paul Stark, Athlone (IE); Catherine Mary Kelly, Athlone (IE); Niall M. Fanning, Rush (IE)

(73) Assignee: Biovail Laboratories, Inc., Barbados (KN)

( * ) Notice: Subject to any disclaimer, the term of this patent is extended or adjusted under 35 U.S.C. 154(b) by 0 days.

(21) Appl. No.: 09/488,103

(22) Filed: Jan. 20, 2000

Related U.S. Application Data
(60) Provisional application No. 60/116,819, filed on Jan. 21, 1999.

(51) Int. Cl.[7] .................................................. A61K 9/16
(52) U.S. Cl. ........................ 424/490; 424/489; 424/464; 424/451
(58) Field of Search .................. 424/489, 490, 424/451, 464, 474, 497

(56) References Cited

U.S. PATENT DOCUMENTS

| | | | |
|---|---|---|---|
| 5,137,733 A | * 8/1992 | Noda et al. | 424/497 |
| 5,580,578 A | * 12/1996 | Oshlack et al. | 424/468 |
| 5,788,987 A | 8/1998 | Busetti et al. | 424/480 |
| 5,830,503 A | 11/1998 | Chen | 424/480 |
| 5,834,023 A | 11/1998 | Chen | 424/497 |
| 5,834,024 A | 11/1998 | Heinicke et al. | 424/497 |
| 5,891,471 A | * 4/1999 | Miller et al. | 424/458 |
| 5,891,474 A | 4/1999 | Busetti et al. | 424/490 |
| 5,897,910 A | 4/1999 | Rosenberg et al. | 427/2.14 |
| 5,939,099 A | 8/1999 | Grabowski et al. | 424/488 |
| 5,965,163 A | 10/1999 | Miller et al. | 424/468 |
| 5,980,882 A | 11/1999 | Eichman | 424/78.12 |
| 6,001,391 A | 12/1999 | Zeidler et al. | 424/467 |
| 6,033,687 A | 3/2000 | Heinicke et al. | 424/497 |
| 6,051,253 A | 4/2000 | Zettler et al. | 424/465 |
| 6,068,855 A | 5/2000 | Leslie et al. | 424/468 |
| 6,120,802 A | 9/2000 | Breitenbach et al. | 424/464 |
| 6,150,424 A | 11/2000 | Breitenbach et al. | 514/772.5 |
| 6,162,467 A | 12/2000 | Miller et al. | 424/468 |
| 6,190,692 B1 | 2/2001 | Busetti et al. | 424/451 |
| 6,214,385 B1 | 4/2001 | Heinicke et al. | 424/497 |
| 6,221,368 B1 | 4/2001 | Breitenbach et al. | 424/400 |
| 6,228,864 B1 | 5/2001 | Smith et al. | 514/288 |
| 6,264,917 B1 | 7/2001 | Klaveness et al. | 424/9.52 |
| 6,270,805 B1 | 8/2001 | Chen et al. | 424/497 |
| 6,284,800 B1 | 9/2001 | Broder et al. | 514/652 |
| 6,303,144 B1 | 10/2001 | Omura | 424/457 |
| 6,350,398 B1 | 2/2002 | Breitenbach et al. | 264/129 |
| 6,358,944 B1 | 3/2002 | Lederman et al. | 514/220 |

FOREIGN PATENT DOCUMENTS

| | | | |
|---|---|---|---|
| EP | 0 463 877 | 1/1992 | A61K/9/54 |
| WO | WO 98/26767 | 6/1998 | A61K/9/50 |
| WO | 98/32425 | 7/1998 | A61K/9/00 |
| WO | WO 98/32426 | * 7/1998 | A61K/9/36 |

OTHER PUBLICATIONS

Handbook for Pharmaceutical Excipients, Second Edition, Polymethacrylates, pp. 362–366, 1994.*

Co–pending U.S. application No. 10/225,543, filed Aug. 22, 2002.

(List continued on next page.)

*Primary Examiner*—Thurman K. Page
*Assistant Examiner*—Robert M. Jones
(74) *Attorney, Agent, or Firm*—Crowell & Moring

(57) ABSTRACT

A multiparticulate bisoprolol formulation for once-daily oral administration, each particle of which comprises a core of bisoprolol or a pharmaceutically acceptable salt thereof surrounded by a polymeric coating, the polymeric coating being effective to achieve an initial lag of bisoprolol release in vivo of at least 4–6 hours following administration and thereafter maintaining therapeutic concentrations of bisoprolol for the remainder of the twenty-four hour period. The formulation can be used for night-time dosing so as to minimize the likelihood of acute cardiovascular occurrences in the well-documented high risk period in the morning.

38 Claims, 3 Drawing Sheets

OTHER PUBLICATIONS

Co–pending U.S. application No. 10/294,693, filed Nov. 15, 2002.

Dorow et al., Effects of Single Oral Doses of Bisoprolol and Atenolol on Airway Function in Nonasthmatic Chronic Obstructive Lung Disease and Angina Pectoris, *Eur. J. Clin. Pharmacol.*, 31(2):143–7: 1986.

Bailliart et al., Effects of Bisoprolol on Local Vascular Resistance, *Eur Heart J*, 8 Suppl M:87–93: 1987.

Haffner et al., A Metabolic Assessment of The Beta$_1$ Selectivity of Bisoprolol, *J. Hum. Hypertens.*, 6(5):397–400, 1992.

Horikiri et al., Pharmacokinetics and Metabolism of Bisoprolol Enantiomers in Humans, *J. Pharm. Sci.*, 87(3): 289–294, 1998.

Janka et al., Infludence of Bisoprolol on Blood Glucose, Glucosuria, and Haemoglobin A$_1$ in Noninsulin–Dependent Diabetics, *J. Cardiovasc. Pharmacol*, 8 Suppl 11:S96–9: 1986.

Kim, et al., Chiral Separation of β–Blockers after Derivatization with (=)–α–Methoxy–α– (trifluoromethyl)phenylacetyl Chloride by Gas Chromatography, *Arch. Pharm. Res.*, 24(5):402–6, 2001.

Kitaori, et al., CsF in Organic Synthesis. The First and Convenient Synthesis of Enantiopure Bisoprolol by Use of Glycidyl Nosylate, *Tetrahedron Lett.*, 39(20), 3173–3176, 1998.

Klockow et al., Studies on The Receptor Profile of Bisoprolol, *Arzneimittelforschung*, 36(2):197–200, 1986.

Nandel et al., Conformational Structure of Some β$_1$–Blockers, Their Partitioning in Lipid and The Role of Parasubstituents, *Ind. J. Biochem. Biophys.*, 32(4); 207–212, 1995.

Nandel et al., Modeling, Design, Chiral Aspects and Role of Para–Substituents in Aryloxypropranolamine Based β–Blockers, *Ind. J. Biochem. Biophys.*, 36(1):29–35, 1999.

Schliep et al., Antagonistic Effects of Bisoprolol on Several β–Adrenoceptor–Mediated Actions in Anaesthetized Cats, *Eur. J. Pharmacol.*, 123(2):253–61, 1986.

Schnabel et al., Binding Properties of β–Blockers at Recobinant β$_1$–, β$_2$–, and β$_3$–Adrenoceptors, *J. Cardiovasc. Pharmacol.*, 36(4):466–71, 2000.

Wellstein et al., Reduction of Excercise Tachycardia in Man after Propranolol, Atenolol and Bisoprolol in Comparison to Beta–Adrenoceptor Occupancy,*Eur. Heart J.*, 8(Suppl. M):3–8, 1987.

"Catecholamines and Sympathomimetic Drugs," Brian B. Hoffman, et al., *Goodman and Gilman's The Pharmacological Basis of Therapeutics, Eighth Edition* (1990), Chapter 10, pp. 187–220.

"Pharmacological Properties of β–adrenoceptor Blocking Drugs," U. Borchard, *J. Clin. Bas. Cardiol.* (1998), 1:5–9.

J. K. Ghali et al, "Metoprolol CR/XL in Female Patients with Heart Failure: Analysis of The Experience In Metoprolol Extended–Release Randomized Intervention Trial in Heart Failure (MERIT–HF)," Circulation, Apr. 2, 2002, vol. 105, No. 13, pp. 1585–1591.

X. Deroubaix et al., "Comparative Bioavailability of a Metoprolol Controlled Release Formula and a Bisoprolol Normal Release Tablet after Single Oral Dose Administration in Healthy Volunteers," International Journal of Clinical Pharmacology and Therapeutics, Feb. 1996, vol. 34, No. 2, pp. 61–70.

G.L. Plasker et al., "Controlled Release Metoprolol Formulations. A review of their Pharmacodynamic and Pharmacokinetic Properties, and Therapeutic Use In Hypertension and Ischaemic Heart Disease," Drugs, Mar. 1992, vol. 43, No. 3, pp. 382–414.

S.P. Glasser et al., "Circadian Heart Rate Response to Chronotherapy Versus Conventional Therapy in Patients with Hypertension and Myocardial Ischemia," Clinical Cardiology, Jul. 2000, vol. 23, No. 7, pp. 524–529.

A. C. Ross et al., "Chronopharmaceutical Drug Delivery From a Pulsatile Capsule Device Based on Programmable Erosion," Journal of Pharmacy and Pharmacology, Aug. 2000, vol. 52, No. 8, pp. 903–909.

M.H. Smolensky et al., "Medical Chronobiology: Concepts and Applications," American Reveiw of Respiratory. Disease, Jun. 1993, vol. 147, No. 6, pp. S2–S19.

G.E. D'Alonzo et al., "Chronophysiologic Determinants of Asthma," Annals New York Acadamy of Science, 1991, vol. 618, pp. 123–139.

M.H. Smolensky et al., "Chronopharmacology and Chronotherapy of Cardio–Vacsular Medications: Relevance to Prevention and Treatment of Coronary Heart Disease," American Heart Journal, 1999, vol. 137, No. 4, pp. S14–S24.

M.C. Cohen et al., "Meta–Analysis of the Morning Excess of Acute Myocardial Infarction and Sudden Cardiac Death," American Journal of Cardiology, 1997, vol. 79, pp. 1512–1515.

W.J. Elliott, "Circadian Variation in the Timing of Stroke Onset: A Meta–Analysis," Stroke, May 1998, vol. 29, No. 5, pp. 992–996.

R. Manfredini et al, "Circadian Variation in Spontaneous Rupture of Abdominal Aorta," The Lancet, Feb. 1999, vol. 353, pp. 643–644.

M.T. Johstone et al., "The Pathophysiology of the Onset of Morning Cardiovascular Events," American Journal of Hypertension, Apr. 1996, vol. 9, No. 4, Part 3, pp. 22S–28S.

M.W. Millar–Craig et al., "Circadian Variation of Blood–Pressure," The Lancet, Apr. 1978, vol. 1, No. 8068, pp. 795–797.

J.A. Staessen et al., "Nocturnal Blood Pressure Fall on Ambulatory Monitoring in a Large International Database," Hypertension, Jan. 1997, vol. 29, No. 1, Part 1, pp. 30–39.

W. J. Elliott, "Circadian Variation in Blood Pressure Implications for the Elderly Patient," American Journal of Hypertension, Feb. 1999, vol. 12, No. 2, Part 2, pp. 43S–49S.

H. Sternberg, "Altered Circadian Rhythm of Blood Pressure in Shift Workers," Journal of Human Hypertension, May 1995, vol. 9, No. 5, pp. 349–353.

I. Kawachi et al., "Prospective Study of Shift Work and Risk of Coronary Heart Disease in Woman," Circulation, Dec. 1, 1995, vol. 92, No. 11, pp. 3178–3182.

H. Boggild et al., "Shift Work, Risk Factors and Cardiovascular Disease," Scandinavian Journal of Work, Environment & Health, Apr. 1999, vol. 25, No. 2, pp. 85–99.

A. F. Khoury et al., "The Early Morning Rise in Blood Pressure Is Related Mainly to Ambulation," American Journal of Hypertension, Jun. 1992, vol. 5, No. 6, Part 1, pp. 339–344.

W. J. Elliott et al., "Drug Delivery Systems For Antihypertensive Agents," Blood Pressure Monitoring, 1997, vol. 2, No. 1, pp. 53–60.

S. K. Gupta et al., "The Effect of Food, Time of Dosing, and Body Position on the Pharmacokinetics and Pharmacokinetics of Verapamil and Norverapamil," The Journal of Clinical Pharmacology, 1995, vol. 35, No. 11, pp. 1083–1093.

* cited by examiner

MULTIPARTICULATE BISOPROLOL FORMULATION

This application claims the benefit of Provisional application Ser. No. 60/116,819, filed Jan. 21, 1999.

This invention relates to a bisoprolol multiparticulate formulation for oral administration and, in particular, to a bisoprolol formulation for chronotherapeutic delivery which can be used for night-time dosing so as to minimise the likelihood of acute cardiovascular occurrences in the well-documented high risk period in the morning.

Bisoprolol (1-[4-[[2-(1-methylethoxy)ethoxy]-methyl] phenoxy]-3-[1-methylethyl)amino]-2-propanol) is a β-adrenoreceptor blocking drug which was first synthesised and developed by E. Merck (U.S. Pat. No. 4,258,062) and was first introduced into the German market in 1986. It is highly β-adrenoreceptor selective and is cleared in equal parts unchanged by the kidneys, and by biotransformation in the liver. Bisoprolol is indicated for therapeutic use in the following areas; the control of arterial hypertension, the management of ischaemic heart disease, the control of some forms of cardiac arrhythmias and in the adjunctive management of hyperthyroidism.

Following oral administration, 90% of bisoprolol is absorbed from the gastrointestinal tract. Peak plasma concentrations are achieved after three hours, (40 ng/ml after a 10 mg dose), and appear not to be affected by concomitant food intake or fasting. The systemic bioavailability of bisoprolol is 90% and hence pre-systemic metabolism is below 10%. The mean plasma half life of 10–12 hours is long compared to other β-blockers. About 50% is excreted unchanged in the urine, the other 50% is biotransformed in the liver with subsequent elimination of pharmacologically inactive metabolites via the kidneys. The pharmacokinetic properties of bisoprolol are not dependent on age or dose in the range 2.5–100 mg.

Generally β-blockers are well tolerated drugs. As far as symptomatic adverse effects are concerned, bisoprolol shows a similar pattern to other β-blockers. Dizziness, headache and tiredness are the most frequent adverse effects spontaneously mentioned by patients treated with bisoprolol. Occasionally cold extremities, sleep disturbances, gastrointestinal upset, weakness of the legs, impotence and sweating have been reported. These effects disappeared in the course of the treatment or when dosage was reduced.

It has been well documented that there is a high risk period in the morning in which there is an increase in acute cardiovascular occurences such as sudden death, myocardial infarction and acute cerebrovascular events. Bisoprolol formulations which are currently dosed in the morning, (with an elimination half life of 10–12 hours), provide therapeutic plasma concentrations over the entire day. However, in order to ensure therapeutic plasma concentrations of bisoprolol on wakening, an evening dosed formulation might be more appropriate.

The aim of the present invention was to achieve such a bisoprolol formulation suitable for night-time dosing with the attendant advantages.

The invention provides a multiparticulate bisoprolol formulation for once-daily oral administration, each particle comprising a core of bisoprolol or a pharmaceutically acceptable salt thereof surrounded by a polymeric coating, said polymeric coating being effective to achieve an initial lag of bisoprolol release in vivo of at least 4–6 hours following administration and thereafter maintaining therapeutic concentrations of bisoprolol for the remainder of the twenty-four hour period.

By lag in bisoprolol release herein is meant zero or minimal release.

The formulation according to the invention enables one to achieve a sufficient delay in release while the patient is asleep, immediate drug release just prior to or following wakening and additionally maintenance of therapeutic concentrations over the dosing interval.

Preferably, the polymeric coating is effective to prevent quantifiable bisoprolol plasma concentrations, such as concentrations of bisoprolol greater than 1 ng/ml, in vivo for a period of at least 3–6 hours.

The initial lag period can be followed by a rapid rise in bisoprolol concentration.

Preferably, the formulation according to the invention contains a pharmaceutically acceptable salt of bisoprolol such as acid addition salts produced by reacting bisoprolol with a suitable acid to produce a pharmaceutically acceptable salt. Suitable salts include those of inorganic acids such as sulphuric acid, nitric acid, hydrogen halide acids, such as hydrochloric acid or hydrobromic acid, and phosphoric acid, such as orthophosphoric acid, and organic acids, in particular aliphatic, alicyclic, araliphatic, aromatic or heterocyclic monobasic or polybasic carboxylic or sulphonic acids, such as formic acid, acetic acid, propionic acid, pivalic acid, diethylacetic acid, malonic acid, succinic acid, pimelic acid, fumaric acid, maleic acid, lactic acid, tartaric acid, malic acid, benzoic acid, salicylic acid, 2-phenyl-propionic acid, citric acid, gluconic acid, ascorbic acid, nicotinic acid, isonicotinic acid, methane- or ethane-sulphonic acid, ethanedisulphonic acid, 2-hydroxyethanesulphonic acid, benzenesulphonic acid, p-tolunesulphonic acid and naphthalene-mono- and di-sulphonic acids.

A preferred salt is bisoprolol fumarate. A particularly preferred salt is bisoprolol hemifumarate, also referred to as bisoprolol fumarate 2:1.

While bisoprolol is typically available in racemic form, formulations according to the invention can contain racemic bisoprolol or enantiomers of bisoprolol either as enantiomeric mixtures or as a substantially purified enantiomer. Thus, as used herein, bisoprolol refers to both racemic and enantiomeric forms of bisoprolol.

Preferably, the bisoprolol active ingredient will comprise 0.5–20%, more especially to 0.5–8%, and most especially 0.5–4% of the total weight of the multiparticulates.

A provisional in vitro dissolution profile for a bisoprolol multiparticulate formulation suitable for night-time dosing was considered to be:

| Time (hours) | % Released |
| --- | --- |
| 0–6 | <10% |
| 6–7 | 40–60% |
| 10 | 65–80% |
| 12 | >80% |
| 14 | >90% |

In practice little correlation was found between in vitro release and in vivo plasma concentration required to achieve the desired therapeutic effects. Although not wishing to be bound by any theoretical explanation of the invention, the delayed release obtained in vivo following night-time dosing is considered to be affected by decreased gastric and possibly intestinal motility during sleep.

A representative in vitro dissolution profile for pH independent multiparticulates is an in vitro dissolution which when measured in a U.S. Pharmacopoeia 2 Apparatus (Paddles) in phosphate buffer at pH 6.8 at 37° C. and 50 rpm substantially corresponds to the following:

(a) from 0% to 10% of the total bisoprolol is released after 2 hours of measurement in said apparatus;

(b) from 0% to 50% of the total bisoprolol is released after 4 hours of measurement in said apparatus; and (c) greater than 50% of the total bisoprolol is released after 10 hours of measurement in said apparatus.

A representative in vitro dissolution profile for pH dependent multiparticulates is an in vitro dissolution which when measured in a U.S. Pharmacopoeia 1 Apparatus (Baskets) at 37° C. and 50 rpm in 0.01 N HCl for the first 2 hours followed by transfer to phosphate buffer at pH 6.8 for the remainder of the measuring period substantially corresponds to the following:

(a) from 0% to 10% of the total bisoprolol is released after 2 hours of measurement in said apparatus;

(b) less than 50% of the total bisoprolol is released after 4 hours of measurement in said apparatus; and (c) greater than 20% of the total bisoprolol is released after 10 hours of measurement in said apparatus.

A sealant or barrier layer can be applied to the core prior to the application of the polymeric coating.

The sealant or barrier layer does not modify the release of bisoprolol significantly. Suitable sealants or barriers are permeable or soluble agents such as hydroxypropyl methylcellulose, hydroxypropyl cellulose, hydroxypropyl ethylcellulose and xanthan gum. Hydroxypropyl methylcellulose is preferred.

Other agents can be added to improve the processability of the sealant or barrier layer. Such agents include talc, colloidal silica, polyvinyl alcohol, titanium dioxide, micronised silica, fumed silica, glycerol monostearate, magnesium trisilicate or magnesium stearate or a mixture thereof.

The sealant or barrier layer can be applied from solution (preferably aqueous) or suspension using a fluidised bed coater (preferably Wurster coating), or in a pan coating system.

Such sealants or barrier coatings are commercially available such as those sold under the Trade Marks OPADRY WHITE Y-1-7000 and OPADRY OY/B/28920 WHITE each of which is available from Colorcon Limited, England.

Preferably, the bisoprolol active ingredient is applied to a non-pareil seed having an average diameter in the range of 0.4–1.1 mm, more especially 0.85–1.00 mm.

The cores can be formed by coating the active ingredient onto inert cores (e.g. non-pareil seeds) to form instant release multiparticulates. The active ingredient can be applied with or without additional excipients onto the inert cores. The active ingredient can be sprayed from solution (preferably aqueous) or suspension using a fluidised bed coater (preferably Wurster coating), or in a pan coating system. Alternatively, the active ingredient can be applied as a powder onto the inert cores using a binder to bind the active ingredient onto the cores. Cores can also be formed by extrusion of the core with suitable plasticisers as described below and any other processing aids as necessary.

A wide range of polymers can be used in the polymer coating. These polymers include enteric polymer coating materials, such as cellulose acetate phthalate, cellulose acetate trimaletate, hydroxy propyl methylcellulose phthalate, polyvinyl acetate phthalate, Eudragit® poly acrylic acid and poly acrylate and methacrylate coatings such as Eudragit® S or Eudragit® L, polyvinyl acetaldiethylamino acetate, hydroxypropyl methylcellulose acetate succinate, cellulose acetate trimellitate, shellac; hydrogels and gel-forming materials, such as carboxyvinyl polymers, sodium alginate, sodium carmellose, calcium carmellose, sodium carboxymethyl starch, polyvinyl alcohol, hydroxyethyl cellulose, methyl cellulose, gelatin, starch and cellulose based cross-linked polymers in general—the degree of cross-linking should be low so as to facilitate adsorption of water and expansion of the polymer matrix, hydoxypropyl cellulose, hydroxypropyl methylcellulose, polyvinylpyrrolidone, cross-linked starch, microcrystalline cellulose, chitin, cellulose acetate cellulose propionate, cellulose acetate propionate, cellulose acetate butyrate, cellulose triacetate, aminoacryl-methacrylate copolymer (Eudragit® RS-PM, Rohm & Haas), pullulan, collagen, casein, agar, gum arabic, sodium carboxymethyl cellulose, carboxymethyl ethyl cellulose, (swellable hydrophilic polymers) poly (hydroxyalkyl methacrylate) (m. wt. ~5 k–5,000 k), polyvinylpyrrolidone (m. wt. ~10 k–360 k), anionic and cationic hydrogels, polyvinyl alcohol having a low acetate residual, a swellable mixture of agar and carboxymethyl cellulose, copolymers of maleic anhydride and styrene, ethylene, propylene or isobutylene, pectin (m. wt. ~30 k–300 k), polysaccharides such as agar, acacia, karaya, tragacanth, algins and guar, polyacrylamides, Polyox® polyethylene oxides (m. wt. ~100 k–5,000 k), AquaKeep® acrylate polymers, diesters of polyglucan, cross-linked polyvinyl alcohol and poly N-vinyl-2-pyrrolidone, sodium starch glucolate (e.g. Explotab®; Edward Mandell C. Ltd.); hydrophilic polymers such as polysaccharides, methyl cellulose, calcium carboxymethyl cellulose, hydroxypropyl methyl cellulose, hydroxypropyl cellulose, hydroxyethyl cellulose, nitrocellulose, carboxymethyl cellulose, cellulose ethers, poly(ethylene terphthalate), poly(vinyl isobutyl ether), polyurethane, polyethylene oxides (e.g. Polyox®, Union Carbide), methyl ethyl cellulose, ethylhydroxy ethylcellulose, cellulose acetate, ethylcellulose, cellulose butyrate, cellulose propionate, gelatin, collagen, starch, maltodextrin, pullulan, polyvinyl pyrrolidone, polyvinyl alcohol, polyvinyl acetate, glycerol fatty acid esters, polyacrylamide, polyacrylic acid, ammonio methacrylate copolymers such as Eudragit® RL or Eudragit® RS (e.g. Eudragit®, Rohm and Haas), other acrylic acid derivatives, sorbitan esters, polydimethyl siloxane, natural gums, lecithins, pectin, alginates, ammonia alginate, sodium, calcium, potassium alginates, propylene glycol alginate, agar, gums: arabic, karaya, locust bean, tragacanth, carrageenans, guar, xanthan, scleroglucan and mixtures and blends thereof.

However, preferably, the polymeric coating contains a major proportion of a pharmaceutically acceptable filmforming polymer which forms an insoluble film of low permeability.

In one embodiment, the polymeric coating contains a minor proportion of a pharmaceutically acceptable filmforming polymer which forms an insoluble film of high permeability.

Further, preferably, the or each polymer is a methacrylic acid co-polymer.

Alternatively, the or each polymer is an ammonio methacrylate co-polymer.

However, a mixture of methacrylic acid co-polymers and ammonio methacrylate co-polymers can be used.

Methacrylic acid co-polymers which include polymers sold under the Trade Marks Eudragit S and Eudragit L by Rohm & Haas are particularly suitable for use in the formulations according to the invention.

These polymers are gastroresistant and enterosoluble polymers. The polymer films are insoluble in pure water and diluted acids. They dissolve at higher pHs, the value of which depends on their content of carboxylic acid. Eudragit S and Eudragit L can be used as single components in the polymer coating Alternatively, the polymers Eudragit S and Eudragit L can be combined in the one coating film in any ratio. By using a combination of the polymers theoretically results in coating films which are soluble at a pH between the pHs at which Eudragit L and Eudragit S are soluble.

Ammonio methacrylate co-polymers which include polymers sold under the Trade Marks Eudragit RS and Eudragit RL by Rohm & Haas are also particularly suitable for use in the formulations according to the invention. These polymers are insoluble in pure water, dilute acids, buffer solutions or digestive fluids over the entire physiological pH range. The films swell in water (and digestive fluids independently of pH). In the swollen state they are then permeable to water and dissolved actives. The permeability of the films depends on the ratio of ethylacrylate (EA), methyl methacrylate (MMA) and trimethylammonioethyl methacrylate chloride (TAMCl) groups in the polymer. Those polymers having EA:MMA:TAMCl ratios of 1:2:0.2 (Eudragit RL) are more permeable than those with ratios of 1:2:0.1 (Eudragit RS). Films of Eudragit RL are described as being "insoluble films of high permeability" and films of Eudragit RS are described as being "insoluble films of low permeability".

Suitably the ammonio methacrylate co-polymers are combined in the ratio of Eudragit RS:Eudragit RL (90:10). However, the two polymers can be combined in a range of ratios. To create the required lag period, the polymers should preferably be combined in ratios in the range of 100:0 to 80:20 Eudragit RS:Eudragit RL, more especially 100:0 to 90:10 Eudragit RS:Eudragit RL, i.e., the major portion of the film coat would be the less permeable polymer Eudragit RS.

The ammonio methacrylate co-polymers can be combined with the methacrylic acid co-polymers within the one film coat in order to achieve a lag. Ratios of ammonio methacrylate co-polymer (particularly Eudragit RS) to methacrylic acid co-polymer in the range of 99:1 to 20:80 can be used to create a lag in release.

The two types of polymers can also be combined in any ratio in separate coats on the cores as hereafter exemplified.

In addition to the Eudragit polymers described above, a number of other such polymers can be used to create a lag in release. These include methacrylate ester co-polymers (e.g. Eudragit NE 30D).

Further information on the Eudragit polymers is to be found in Chemistry and Application Properties of Polymethacrylate Coating Systems" from "Aqueous Polymeric Coatings for Pharmaceutical Dosage Forms" edited by James McGinity (Marcel Dekker Inc., New York) pg 109–114).

Preferably, the polymeric coating includes one or more soluble excipients so as to increase the permeability of the coating.

Suitably, the or each soluble excipient is selected from a soluble polymer, a surfactant, an alkali metal salt, an organic acid, a sugar and a sugar alcohol.

Such soluble excipients include polyvinyl pyrrolidone, polyethylene glycol, sodium chloride, surfactants such as sodium lauryl sulphate and polysorbates, organic acids such as acetic acid, adipic acid, citric acid, fumaric acid, glutaric acid, malic acid, succinic acid, and tartaric acid and sugars such as dextrose, fructose, glucose, lactose and sucrose, and sugar alcohols such as lactitol, maltitol, mannitol, sorbitol and xylitol, xanthan gum, dextrins, poloxamers and maltodextrins, Polyvinyl pyrrolidone, mannitol and polyethylene glycol are the preferred soluble excipients.

Preferably, the soluble excipient is used in an amount of from 1% to 10% by weight, based on the total dry weight of the polymer.

The polymeric coating can also include one or more auxiliary agents selected from a filler, a plasticiser and an anti-foaming agent.

Representative fillers include talc, fumed silica, glyceryl monostearate, magnesium stearate, calcium stearate, kaolin, colloidal silica, gypsum, micronised silica and magnesium trisilicate.

Talc is the preferred filler.

The quantity of filler used is from about 2% to about 300% by weight, preferably 20 to 100%, based on the total dry weight of the polymer.

The coatings can also include a material that improves the processing of the polymers. Such materials are generally referred to as "plasticisers" and include, for example, adipates, azelates, benzoates, citrates, isoebucates, phthalates, sebacates, stearates and glycols.

Representative plasticisers include acetylated monoglycerides; butyl phthalyl butyl glycolate; dibutyl tartrate; diethyl phthalate; dimethyl phthalate; ethyl phthalyl ethyl glycolate; glycerin; ethylene glycol, propylene glycol; triacetin citrate; triacetin; tripropinoin; diacetin; dibutyl phthalate; acetyl monoglyceride; polyethylene glycols; castor oil; triethyl citrate; polyhydric alcohols, acetate esters, gylcerol triacetate, acetyl triethyl citrate, dibenzyl phthalate, dihexyl phthalate, butyl octyl phthalate, diisononyl phthalate, butyl octyl phthalate, dioctyl azelate, epoxidised tallate, triisoctyl trimellitate, diethylhexyl phthalate, di-n-octyl phthalate, di-i-octyl phthalate, di-i-decyl phthalate, di-n-undecyl phthalate, di-n-tridecyl phthalate, tri-2-ethylhexyl trimellitate, di-2-ethylhexyl adipate, di-2-ethylhexyl sebacate, di-2-ethylhexyl azelate, dibutyl sebacate, glyceryl monocaprylate and glyceryl monocaprate.

Dibutyl sebacate is the preferred plasticiser.

The amount of plasticiser to be used in the coating is preferably from about 10% to 50%, most preferably about 20%, based on the weight of the dry polymer.

An example of an anti-foaming agent is Simethicone. The amount of anti-foaming agent to be used in the coating is preferably from 0% to 0.5% of the final formulation.

The amount of coating to be used in forming the multiparticulates will be determined by the desired delivery properties, including the amount of drug to be delivered, the time delay desired, and the size of the multiparticulates. The coating polymers will be coated to 10 to 100% weight gain on the cores, preferably 25–70% polymer weight gain. The coating on the multiparticulates providing the delay, including all solid components of the coating such as co-polymer, filler, plasticiser and optional additives and processing aids, is from about 11% to 450% weight gain on the cores, preferably 30% to 160% weight gain. The polymer layer can be coated by any known method, including spray application. Spraying can be carried out using a fluidised bed coater (preferably Wurster coating), or in a pan coating system.

The coated cores are dried or cured after application of the polymer layer(s). "Curing" means that the multiparticulates are held at a controlled temperature for a time sufficient to provide stable release rates. Curing can be performed for example in an oven or in a fluid bed drier. Curing can be carried out at any temperature above room temperature.

A sealant or barrier layer can be applied to the polymeric coating.

The sealant or barrier layer, when such is present, can be formed of any of the materials hereinabove specified for the sealant or barrier layer applied to the core.

The sealant or barrier layer may be applied to the polymeric coating to prevent agglomeration of the multiparticulates.

The invention also provides an oral dosage form containing a multiparticulate bisoprolol formulation as hereinabove defined, which is in the form of caplets, capsules, particles for suspension prior to dosing, sachets or tablets.

When the dosage form is in the form of tablets, the tablets are preferably selected from disintegrating tablets, fast dissolving tablets, effervescent tablets, fast melt tablets and mini-tablets.

The dosage form can be of any shape suitable for oral administration of a drug, such as spheroidal, cube-shaped oval or ellipsoidal.

The dosage form will suitably contain from 1–30 mg, preferably 1.25–10 mg, of active ingredient. The dosage forms will be prepared from the multiparticulates in a manner known per se, including additional excipients, where required.

Figure 1:
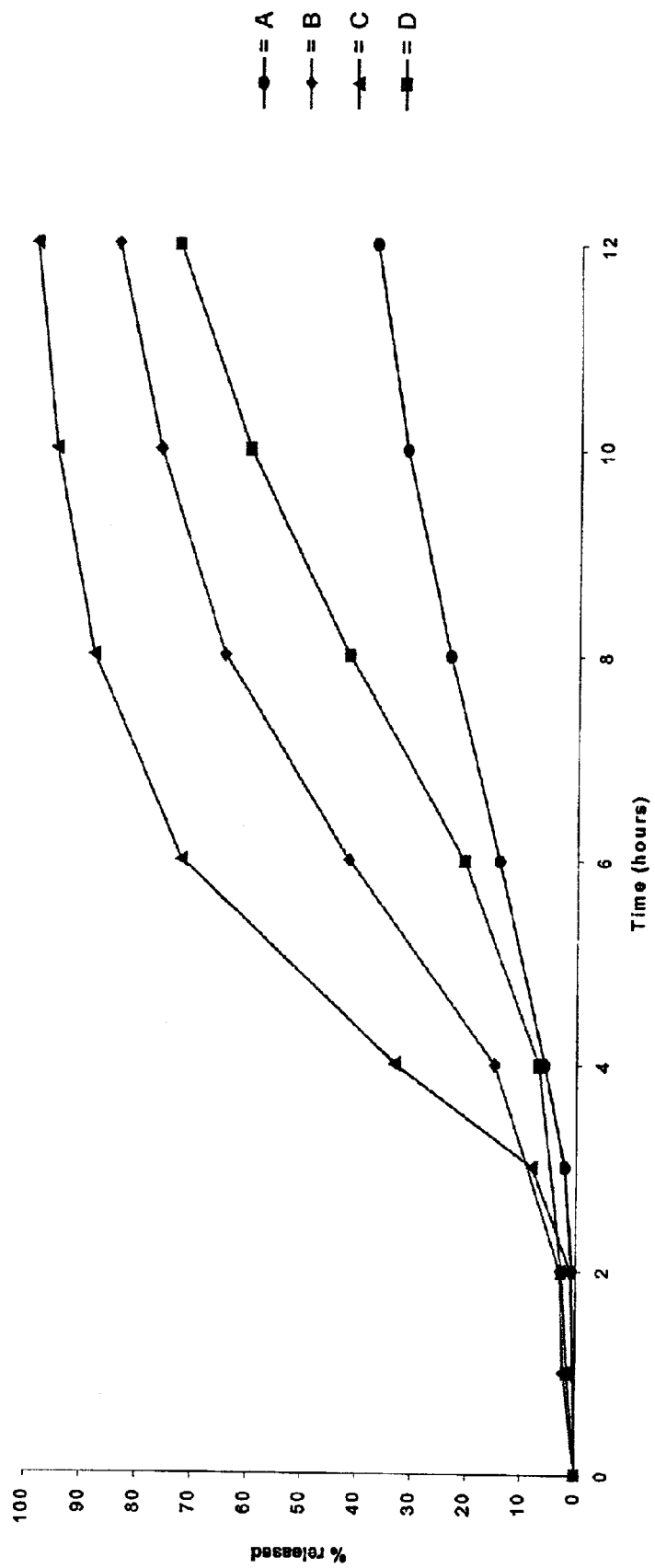
FIG. 1 is a graph of % bisoprolol released versus time (hours) for encapsulated multiparticulates as described in Example 12 over a 12 hour period.

The invention will be further illustrated by the following Examples.

EXAMPLE 1

Preparation of Layered Multiparticulates Containing Bisoprolol Fumarate 2:1

A solution of bisoprolol fumarate 2:1 was prepared as follows. To 529.2 g of purified water were added 180 g of bisoprolol fumarate 2:1. The mixture was stirred for 10 minutes to dissolve the drug. 10.8 g of talc USP (Whitaker, Clark and Daniels Inc., South Plainfield, N.J., USA) were added to the solution and the mixture was stirred for 20 min.

The suspension was sprayed onto 0.85–1.00 mm non-pareil seeds (NP Pharma SA, France) in a fluid bed apparatus (GPCG-3, Glatt) using Wurster coating. The drug was layered onto the non-pareil seeds to give a 5% drug weight gain. The spray rate for drug layering was 1.5–3.6 g/min/kg, the inlet temperature was 50° C. and the non-pareils were maintained at 37–42° C. The drug loaded instant release multiparticulates were cooled in the Glatt GPCG-3 for 10 minutes. The multiparticulates were screened to remove oversized beads and fine material.

EXAMPLE 2

Preparation of Eudragit RS:RL (90:10) Coated Multiparticulates Containing Bisoprolol Fumarate 2:1

A Eudragit RS:Eudragit RL (90:10) aqueous dispersion was prepared as follows: 0.5 g of Simethicone emulsion USP (OSI Specialities, Belgium) and 300 g of talc USP were added with mixing to 1139.5 g of purified water. The mixture was stirred for 15 minutes. 900 g of Eudragit RS 30D and 100 g of Eudragit RL 30D (ammonio methacrylate co-polymers in the form of aqueous dispersions from Rohm Pharma, Germany) were added to the mixture and stirred for 20 minutes. 60 g of dibutyl sebacate (Morflex Inc., Greensboro, N.C., USA) were added to the mixture and stirred for 20 minutes. The aqueous dispersion was screened through a 500 μm sieve.

The resulting combined dispersion was sprayed onto instant release multiparticulates prepared according to Example 1, using a fluid bed apparatus as used in Example 1. Spray rate was 3–10 g/min/kg, and the inlet temperature was 45–50° C. The instant release multiparticulates were maintained at 30–40° C. and the air volume was 150–190 m³/h. A polymer coating of 40.08% polymer weight gain was coated onto the instant release multiparticulates. The coated multiparticulates were cooled in the Glatt GPCG-3 for 30 minutes post coating, then dried/cured in the following manner:

Phase 1 50° C. phase: 50° C. for 11 h. 25 min., temperature dropped (steamer down) to a low of 40° C. over 1 h. 35 min. Temperature fluctuated between 40–56° C. for 30 min. Temperature remained at 50° C. for a further 34 h. 30 min;

Phase 2: 35° C. phase: Temperature dropped to 35° C. over 2 h. 25 min. Temperature remained at 35° C. for a further 29 h. 9 min. (Total time at 50° C.—45 h. 55 min. Total time at 35° C.—29 h. 9 min.)

The multiparticulates were screened to remove oversized multiparticulates and fine material.

EXAMPLE 3

Preparation of Eudragit RS:Eudragit RL (90:10) Coated Multiparticulates Containing Bisoprolol Fumarate 2:1

Bisoprolol instant release multiparticulates prepared according to Example 1) were coated with the Eudragit RS:Eudragit RL (90:10) aqueous dispersions (prepared according to Example 2) to a higher polymer weight gain of 50.03%. The multiparticulates were cured in the following manner:

50° C. for 8 h. 45 min., temperature dropped (steamer down) to a low of 30° C. over 5 h. 55 min. Oven reset and remained at 50° C. for a further 24 h. 25 min. Oven reset again (to account for loss of hours when steamer down). Temperature fluctuated between 38 and 53° C. for 1 h. 45 min. Temperature remained at 50° C. for 15 h. 38 min. Temperature ramped down to 29° C. over the next 5 hr 30 mins.

(Total time at 50° C.—48 h. 48 min).

The multiparticulates were screened as described in Example 2.

EXAMPLE 4

Preparation of Eudragit L Overcoated Multiparticulates Containing Bisoprolol Fumarate 2:1

Bisoprolol instant release multiparticulates (prepared according to Example 1) were coated with Eudragit RS:Eudragit RL (90:10) aqueous dispersion (prepared according to Example 2) to a polymer weight gain of 29.93%. The multiparticulates were cured and screened as described in Example 2.

A Eudragit L polymer solution was then prepared as follows: 120 g of purified water, 1705 g of isopropyl alcohol and 50 g of dibutyl sebacate were mixed together and stirred for 10 minutes. 125 g of talc USP was added to the mixture and stirred for 15 minutes. 2000 g of Eudragit L 12.5 (solution of methacrylate co-polymer from Rohm Pharma, Germany) was added and stirred for 15 minutes.

The resulting polymer solution was sprayed onto bisoprolol multiparticulates coated to 29.93% polymer weight gain with Eudragit RS:Eudragit RL (90:10) polymer coat described above in this Example. The Eudragit L solution was coated with a fluid bed apparatus (Glatt GPCG-3) using Wurster coating. Spray rate was 6–16 g/min /kg, and the inlet temperature was 35–40° C. The multiparticulates were maintained at 30–32° C. during coating and the air volume was 120–140 m³/h. A polymer coating of 20.05% Eudragit L weight gain was coated onto the Eudragit RS:Eudragit RL (90:10) coated multiparticulates. The Eudragit L coated multiparticulates were cured in the Glatt GPCG-3 for 60 minutes post coating. The multiparticulates were screened to remove oversized multiparticulates and fine material.

The multiparticulates were screened to remove oversized multiparticulates and fine material.

EXAMPLE 6

In vitro Dissolution of Multiparticulates

Dissolution details for the multiparticulates produced as described in Examples 2 to 5 above are shown in Table 1 below. Multiparticulates manufactured as described in Examples 2 and 3 were tested in phosphate buffer pH 6.8 in USP II apparatus with paddles at 50 rpm. Multiparticulates manufactured as described in Examples 4 and 5 were tested in 0.01N HCl for 2 h. then transferred to phosphate buffer pH 6.8 for the remainder of the testing interval. Baskets were used rather than paddles for Examples 4 and 5, at 50 rpm.

TABLE 1

Dissolution profiles for multiparticulates manufactured as described in Examples 2 to 5

| Example 2 | | Example 3 | | Example 4 | | Example 5 | |
|---|---|---|---|---|---|---|---|
| 40.08% Eudragit RS:Eudragit RL (90:10) coated multiparticulates | | 50.03% Eudragit Rs:Eudragit RL (90:10) coated multiparticulates | | 20.05% Eudragit L overcoated multiparticulates | | 35.09% Eudragit S coated multiparticulates | |
| Dissolution profile | | | | | | | |
| Time (hours) | % released | Time (hours) | % released | Time (hours) | % released | Time (hours) | % released |
| 1 | 1.8 | 1 | 1.9 | 2 | 0 | 2 | 0 |
| 2 | 3.5 | 2 | 2.6 | 3 | 8.5 | 3 | 1.5 |
| 4 | 27.3 | 4 | 10.0 | 4 | 29.0 | 4 | 4.7 |
| 6 | 58.2 | 6 | 33.9 | 6 | 67.2 | 6 | 13.0 |
| 8 | 76.2 | 8 | 58.5 | 8 | 84.2 | 8 | 20.6 |
| 10 | 86.3 | 10 | 74.7 | 10 | 91.7 | 10 | 28.0 |
| 12 | 91.0 | 12 | 83.9 | 12 | 96.6 | 12 | 33.4 |
| 22 | 99.1 | 22 | 100.3 | | | 24 | 51.4 |

EXAMPLE 5

Preparation of Eudragit S Coated Multiparticulates Containing Bisoprolol Fumarate 2:1

A Eudragit S solution was prepared as follows: 300 g of purified water and 4262.5 g of isopropyl alcohol were stirred together for 5 minutes. 125 g of dibutyl sebacate were added and the mixture stirred for 5 minutes. 312.5 g of talc USP were added to the mixture and stirred for 15 minutes. 5000 g of Eudragit S 12.5 (solution of methacrylate co-polymer from Rohm Pharma, Germany) was added and stirred for 30 minutes.

The resulting solution was sprayed onto instant release multiparticulates prepared according to Example 1, using a fluid bed apparatus as used in Example 1. Spray rate was 3–12 g/min/kg, and the inlet temperature was 38–40° C. The instant release multiparticulates were maintained at 30–35° C. and the air volume was 130–160 m³/hr. A polymer coating of 35.09% polymer weight gain was coated onto the instant release multiparticulates. The coated multiparticulates were cooled in the Glatt GPCG-3 for 10 minutes post coating, then dried/cured in the following manner:

15 h. at 40° C. Cooled to 34° C. over 1 h. 45 min.
  Remained at 34–35° C. for 7 h. 15 min.

In addition to the formulations described in Examples 1 to 6 above, different polymer coating combinations were coated onto instant release multiparticulates manufactured as described in Example 1 above using the GPCG-3 or the Uni-Glatt. Examples of the additional formulations manufactured are described below.

EXAMPLE 7

Preparation of Eudragit RS:Eudragit RL (97.5:2.5) Coated Multiparticulates Containing Bisoprolol Fumarate 2:1

A Eudragit RS:Eudragit RL (97.5:2.5) aqueous dispersion was prepared as follows: 0.8 g of Simethicone emulsion USP (OSI Specialities, Belgium) and 480 g of talc were added with mixing to 1823.2 g of purified water. The mixture was stirred for 15 minutes. 1560 g of Eudragit RS 30D and 40 g of Eudragit RL 30D (ammonio methacrylate co-polymers in the form of aqueous dispersions from Rohm Pharma, Germany) were added to the mixture and stirred for 10 minutes. 96 g of dibutyl sebacate (Morflex Inc., Greensboro, N.C., USA) were added to the mixture and stirred for 15 minutes.

The resulting combined dispersion was sprayed onto instant release multiparticulates prepared according to Example 1 (but manufactured on the Uni-Glatt), using a fluid bed apparatus (Uni-Glatt) using Wurster coating. Spray rate was 3.2–8.6 g/min/kg, and the inlet temperature was 34–46° C. The outlet air flap setting on the Uni-Glatt was maintained at a setting of 50. A polymer coating of 20.41% polymer weight gain was coated onto the instant release multiparticulates. The coated multiparticulates were cooled in the Uni-Glatt for 30 minutes post coating, then dried/cured in an oven at 50° C. for 86 h. The multiparticulates were screened to remove oversized multiparticulates and fine material.

EXAMPLE 8

Preparation of Eudragit RS:Eudragit RL (95:5) Coated Multiparticulates Containing Bisoprolol Fumarate 2:1

A Eudragit RS:Eudragit RL (95:5) aqueous dispersion was prepared as follows: 0.6 g of Simethicone emulsion USP (OSI Specialities, Belgium) and 360 g of talc were added with mixing to 1367.4 g of purified water. The mixture was stirred for 15 minutes. 1140 g of Eudragit RS 30D and 60 g of Eudragit RL 30D (ammonio methacrylate co-polymers in the form of aqueous dispersions from Rohm Pharma, Germany) were added to the mixture and stirred for 10 minutes. 72 g of dibutyl sebacate (Morflex Inc., Greensboro, N.C., USA) were added to the mixture and stirred for 15 minutes.

The resulting combined dispersion was sprayed onto instant release multiparticulates prepared according to Example 1 (but manufactured on the Uni-Glatt), using a fluid bed apparatus (Uni-Glatt) using Wurster coating. Spray rate was 1.4–10.7 g/min/kg, and the inlet temperature was 38–52° C. The outlet air flap setting on the Uni-Glatt was maintained at a setting of 50. A polymer coating of 20.60% polymer weight gain was coated onto the instant release multiparticulates. The coated multiparticulates were cooled in the Uni-Glatt for 30 minutes post coating, then dried/cured in an oven at 50° C. for 48 h. The multiparticulates were screened to remove oversized multiparticulates and fine material.

EXAMPLE 9

Preparation of Eudragit RS:PVP K-30 (95:5) Coated Multiparticulates Containing Bisoprolol Fumarate 2:1

A Eudragit RS:PVP K-30 (95:5) aqueous dispersion was prepared as follows: 0.6 g of Simethicone emulsion USP (OSI Specialities, Belgium) and 18 g of Kollidon 30 (BASF) were added with mixing to 1409.4 g of purified water. The mixture was stirred for 10 minutes. 360 g of talc USP were added to the mixture and stirred for 15 minutes. 1140 g of Eudragit RS 30D (ammonio methacrylate co-polymer in the form of aqueous dispersion from Rohm Pharma, Germany) was added to the mixture and stirred for 10 minutes. 72 g of dibutyl sebacate (Morflex Inc., Greensboro, N.C., USA) were added to the mixture and stirred for 15 minutes.

The resulting combined dispersion was sprayed onto instant release multiparticulates prepared according to Example 1, using a fluid bed apparatus as used in Example 1. Spray rate was 4.2–15.2 g/min/kg, and the inlet temperature was 48–54° C. The instant release multiparticulates were maintained at 37–44° C. and the air volume was 147–231 m³/h. A polymer coating of 20.86% polymer weight gain was coated onto the instant release multipar-ticulates. The coated multiparticulates were cooled in the Glatt GPCG-3 for 30 minutes post coating, then dried/cured in an oven at 50° C. for 46 h. The multiparticulates were screened to remove oversized multiparticulates and fine material.

EXAMPLE 10

In vitro Dissolution of Multiparticulates

Dissolution details for the multiparticulates produced as described in Examples 7 to 9 above are shown in Table 2 below. All multiparticulates manufactured as described in these Examples were tested in phosphate buffer pH 6.8 in USP 2 apparatus with paddles at 50 rpm.

TABLE 2

Dissolution profiles for multiparticulates manufactured as described in Examples 7 to 9

| Example 7 20.41% Eudragit RS:Eudragit RL (97.5:2.5) coated multiparticulates | | Example 8 20.60% Eudragit RS:Eudragit RL (95:5) coated multiparticulates | | Example 9 20.86% Eudragit RS:PVP K-30 (95:5) coated multiparticulates | |
|---|---|---|---|---|---|
| Dissolution profile | | | | | |
| Time (hours) | % released | Time (hours) | % released | Time (hours) | % released |
| 1 | 1.3 | 1 | 0.8 | 1 | 1.7 |
| 2 | 2.4 | 2 | 1.4 | 2 | 2.6 |
| 3 | 3.8 | 3 | 2.9 | 4 | 9.1 |
| 4 | 5.9 | 4 | 6.1 | 6 | 20.8 |
| 5 | 8.8 | 5 | 10.9 | 8 | 32.2 |
| 6 | 12.3 | 6 | 17.0 | 10 | 40.6 |
| 7 | 15.8 | 7 | 26.4 | 12 | 47.2 |
| 8.5 | 21.2 | 8.5 | 38.1 | | |
| 10 | 27.4 | 10 | 48.7 | | |

Combination of one or more types of coated multiparticulates, such as those described in Examples 2–5 and 7–9, may also be used to form suitable formulations. However, a two component system formed by mixing two populations of coated multiparticulates chosen from those in Examples 2–5 and 7–9 appears to offer no particular advantage over a single component system with respect to achieving a suitable in vitro release.

Examples 11 and 12 are examples of bisoprolol delayed release multiparticulates including a sealant or barrier layer.

EXAMPLE 11

Step A:

Preparation of Layered Multiparticulates Containing Bisoprolol

A solution of bisoprolol was prepared as follows. To 529.2 g of purified water were added 180 g of bisoprolol fumarate 2:1. The mixture was stirred for 10 minutes to dissolve the drug. 10.8 g of talc USP (Whitaker, Clark and Daniels Inc., South Plainfield, N.J., USA) were added to the solution and the mixture was stirred for 20 minutes.

The suspension was sprayed onto 0.85–1.00 mm non-pareil seeds (NP Pharma SA, France) in a fluid bed apparatus (GPCG-3, Glatt) using Wurster coating. The drug was layered onto the non-pareil seeds to give a 5% drug weight gain. The spray rate for drug layering was 1.5–3.6 g/min/kg, the inlet temperature was 50° C. and the non-pareils were maintained at 37–42° C. The drug loaded instant release multiparticulates were cooled in the Glatt GPCG-3 for 10 minutes. The multiparticulates were screened to remove oversized beads and fine material.

Step B:

Coating Instant Release Multiparticulates with Barrier Layer

A suspension of Opadry White in water was prepared as follows: To 900.0 g of purified water were added 100.0 g of Opadry White Y-1-7000 (Colorcon Ltd, England) with stirring. The mixture was stirred for a further 45 minutes to disperse the Opadry White. The suspension was screened through a 500 μm screen.

The suspension was sprayed onto the instant release bisoprolol multiparticulates (manufactured as described in Step A) in a fluid bed apparatus (GPCG-3, Glatt) using Wurster coating. The Opadry White was layered onto 2.2 Kg of instant release multiparticulates to give 2% solids weight gain. The spray rate for coating with the Opadry White suspension was 1.7–2.5 g/min/kg, the inlet temperature was 44–47° C. and the non-pareils were maintained at 36–39° C. The Opadry coated multiparticulates were cooled in the Glatt GPCG-3 for 10 minutes. The multiparticulates were screened to remove oversized beads and fine material.

Step C:

Preparation of Eudragit RS:Eudragit RL (90:10) Coated Multiparticulates Containing Bisoprolol A Eudragit RS:Eudragit RL (90:10) aqueous dispersion was prepared as follows: 1.6 g of Simethicone emulsion USP (OSI Specialities, Belgium) and 960 g of talc USP were added with mixing to 3646.4 g of purified water. The mixture was stirred for 15 minutes. 2880 g of Eudragit RS 30D and 320 g of Eudragit RL 30D (ammonio methacrylate co-polymers in the form of aqueous dispersions from Rohm Pharma, Germany) were added to the mixture and stirred for 20 minutes. 192 g of dibutyl sebacate (Morflex Inc., Greensboro, N.C., USA) were added to the mixture and stirred for 20 minutes. The aqueous dispersion was screened through a 500 μm sieve.

The resulting combined dispersion was sprayed onto the 2% Opadry White coated multiparticulates prepared according to Step B, using a fluid bed apparatus as used in Step A. Spray rate was 2.7–10.9 g/min/kg, and the inlet temperature was 45–48° C. The Opadry White coated multiparticulates were maintained at 28–40° C. and the air volume was 149–169 m³/hr. A polymer coating of 29.96% polymer weight gain was coated onto the Opadry White multiparticulates. The coated multiparticulates were cooled in the Glatt GPCG-3 for 30 minutes post coating.

A further 10.65% polymer weight gain was achieved by continuing the coating of the Eudragit RS:Eudragit RL (90:10) aqueous dispersion onto 1.00 Kg the 29.96% polymer coated multiparticulates in the Glatt GPCG-3. Spray rate was 7.7–11.3 g/min 1 kg, and the inlet temperature was 46–49° C. The 29.96% polymer coated multiparticulates were maintained at 32.9–40.4° C. and the air volume was 126–136 m³/hr. The total polymer coating applied to the Opadry White coated multiparticulates at the end of this process was 40.61% polymer weight gain. The coated multiparticulates were cooled in the Glatt GPCG-3 for 30 minutes post coating. The coated multiparticulates were dried/cured in an oven at the following temperatures and times:

Phase 1: 50° C. for 33 hr 25 minutes, temperature dropped to a low of 32° C. for 2 hours, temperature returned to 50° C. for a further 12 h. 35 min. Temperature dropped to 35° C. over 2 hours (problem with oven—temperature fell below 35° C. to low of 24° C.—below 35° C. for 17.45 hours). Returned to 35° C. for further 28 hours 45 minutes.

The multiparticulates were screened to remove oversized multiparticulates and fine material.

Dissolution results for 40.61% Eudragit RS:Eudragit RL (90:10) coated multiparticulates manufactured to include a barrier coat of Opadry White are shown in Table 3.

| Dissolution method | |
|---|---|
| Apparatus: | USP 2 apparatus (Paddles) |
| Speed: | 50 rpm |
| Medium: | Phosphate buffer pH 6.8 at 37° C. |

TABLE 3

40.61% Eudragit RS:Eudragit RL (90:10) coated multiparticulates with Opadry White barrier layer
Dissolution profile

| Time (hours) | % bisoprolol released |
|---|---|
| 1 | 2.3 |
| 2 | 13.4 |
| 4 | 61.5 |
| 6 | 82.4 |
| 8 | 92 |
| 10 | 96.1 |
| 12 | 98.6 |
| 22 | 102.7 |

EXAMPLE 12

Step A

Preparation of Layered Multiparticulates Containing Bisoprolol

As described under Example 11, Step B.

Step B

Coating Instant Release Multiparticulates with Barrier Layer

A suspension of Opadry Aqueous Moisture Barrier in water was prepared as follows: To 1350 g of purified water were added 150.0 g of Opadry OY/B/28920 White (Colorcon Ltd, England) with stirring. The mixture was stirred for a further 45 minutes to disperse the Opadry White. The suspension was screened through a 500 μm screen.

The suspension was sprayed onto the instant release bisoprolol multiparticulates (manufactured as described in Step A) in a fluid bed apparatus (GPCG-3, Glatt) using Wurster coating. The Opadry Aqueous Moisture Barrier was layered onto 1.5 Kg of instant release multiparticulates to give 3% solids weight gain. The spray rate for coating with the Opadry Aqueous Moisture Barrier suspension was 2.7–4.6 g/min/kg, the inlet temperature was 49–55° C. and the non-pareils were maintained at 39.9–44.9° C. during the coating process. The Opadry coated multiparticulates were dried in the Glatt GPCG-3 for 5 minutes, then cooled for 16 minutes in the Glatt. The multiparticulates were screened to remove oversized beads and fine material.

Step C

Preparation of Eudragit RS:Eudragit RL (90:10) Coated Multiparticulates Containing Bisoprolol A Eudragit RS:Eudragit RL (90:10) aqueous dispersion was prepared as follows: 0.9 g of Simethicone emulsion USP (OSI Specialities, Belgium) and 108 g of Dibutyl sebacate (Morflex Inc., Greensboro, N.C., USA) were added with mixing to 2051.1 g of purified water. The mixture was stirred for 10 minutes. 540 g of Talc USP were added to the mixture and stirred for 15 minutes. 1620 g of Eudragit RS 30D and 180 g of Eudragit RL 30D (ammonio methacrylate co-polymers in the form of aqueous dispersions from Rohm Pharma, Germany) were added to the mixture and stirred for 15 minutes.

The resulting combined dispersion was sprayed onto the 3% Opadry Aqueous Moisture Barrier coated multiparticulates prepared according to Step B, using a fluid bed apparatus as used in Step A. Spray rate was 5.0–11.7 g/min/kg, and the inlet temperature was 45–48° C. The Opadry Aqueous Moisture Barrier coated multiparticulates were maintained at 32.8–40.9° C. and the air volume was 119–158 m$^3$/hr. A polymer coating of 29.84% polymer weight gain was coated onto the Opadry White multiparticulates. The coated multiparticulates were dried post coating in the Glatt GPCG-3 for 1 hour at inlet temperature of 45–55° C. then cooled for 5 minutes. The multiparticulates were then dried in an oven for 48 hours at 50° C. The temperature dropped to 35° C. over the next 1.5 hours, then the temperature was maintained at 35° C. for the next 13.75 hours. The multiparticulates were screened to remove oversized multiparticulates and fine material.

Dissolution results for 29.84% Eudragit RS:Eudragit RL (90:10) coated multiparticulates manufactured to include a barrier coat of Opadry Aqueous Moisture Barrier are shown in Table 4.

Dissolution Method

Apparatus: USP 2 apparatus (Paddles)

Speed: 50 rpm

Medium: Phosphate buffer pH 6.8 at 37° C.

TABLE 4

29.84% Eudragit RS:Eudragit RL (90:10) coated multiparticulates Dissolution profile

| Time (hours) | % bisoprolol released |
| --- | --- |
| 1 | 1.6 |
| 2 | 7.1 |
| 4 | 48.2 |
| 6 | 73.7 |
| 8 | 85.0 |
| 10 | 91.0 |
| 12 | 93.8 |
| 22 | 99.2 |

EXAMPLE 13

Preparation of Capsules Containing 5 mg of Bisoprolol Fumarate 2:1

Coated multiparticulates manufactured as described in Examples 2–5 were encapsulated in size 2 hard gelatin capsules to give dosage forms containing the equivalent of 5 mg of bisoprolol fumarate 2:1. The dissolution methods used for the encapsulated multiparticulates were as follows:

EXAMPLES 2 and 3

| Apparatus: | USP 2 apparatus (Paddles) |
| --- | --- |
| Speed: | 50 rpm |
| Medium: | Phosphate buffer pH 6.8 at 37° C. |

EXAMPLES 4 and 5

| Apparatus: | USP 1 apparatus (Baskets) |
| --- | --- |
| Speed: | 50 rpm |
| Medium: | 0.01N HCl for the first 2 hours. Then transferred to phosphate buffer pH 6.8 for the remainder of the testing period. Temperature 37° C. |

Figure 2:
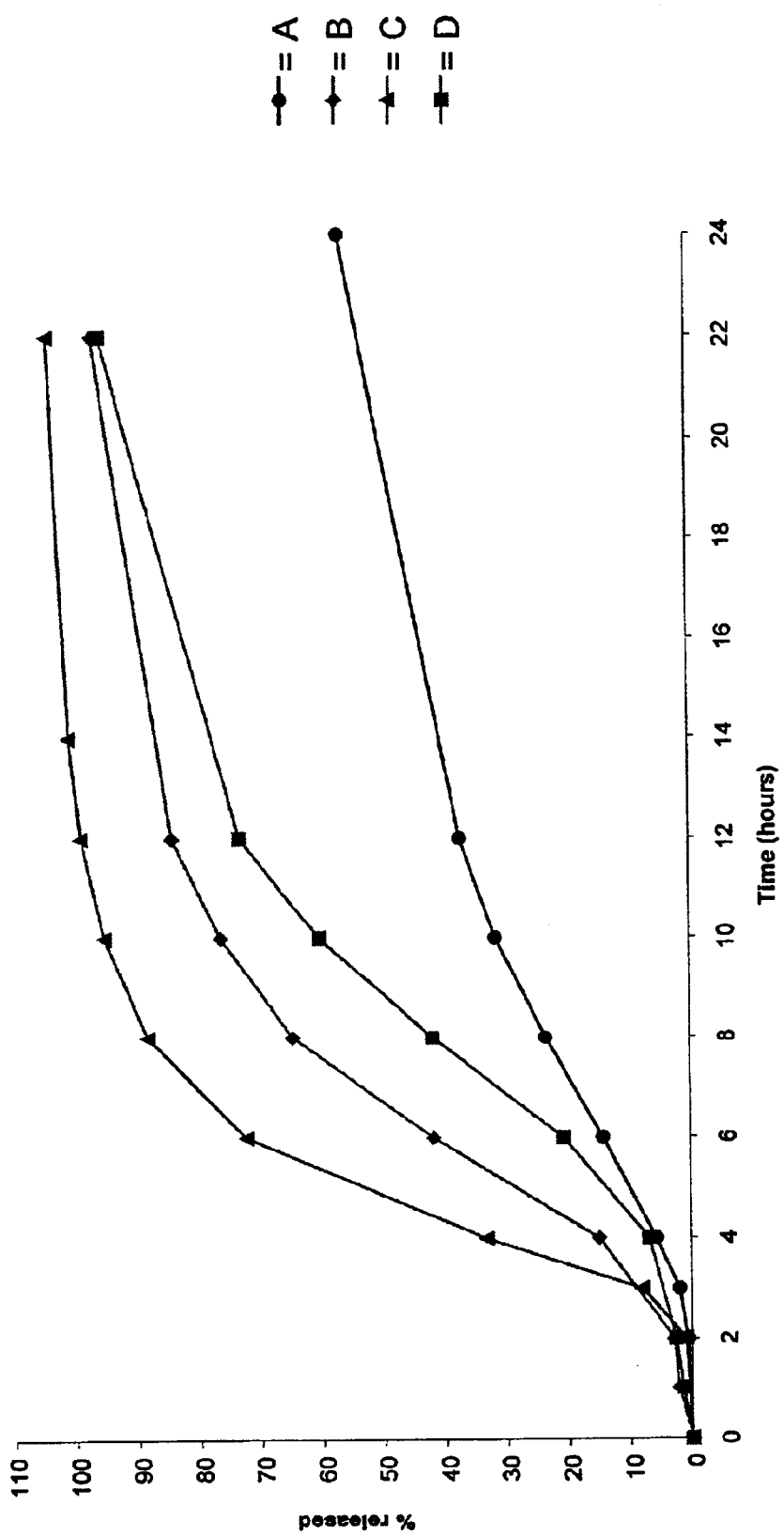
FIG. 2 is a graph of % bisoprolol released versus time (hours) for encapsulated multiparticulates as described in Example 12 over a 24 hour period.

The results are shown in FIGS. 1 and 2 wherein:

A=The product of Example 5

B=The product of Example 2

C=The product of Example 4

D=The product of Example 3.

EXAMPLE 14

Biostudy

An open label, single dose, five treatment, five period, balanced, randomised crossover study was designed to compare the bioavailability of the formulations described in Examples 2–5 and as encapsulated according to Example 13 (5 mg bisoprolol fumarate 2:1) relative to a reference Concor® 5 mg tablet (E. Merck). Fifteen healthy male volunteers were dosed as one group with each volunteer being dosed on five occasions with at least a seven-day washout period between each dose. The volunteers fasted from food and beverages other than water for at least four hours prior to dosing in each treatment period and water was proscribed one hour before and one hour after dosing. The Volunteers were fed an evening meal (approximately 17:00 hours) and dosing occurred at night (approximately 22.00 hours) followed by at least a 10-hour fast. Venous blood specimens were obtained from the volunteers at regular time intervals following each dosing.

Figure 3:
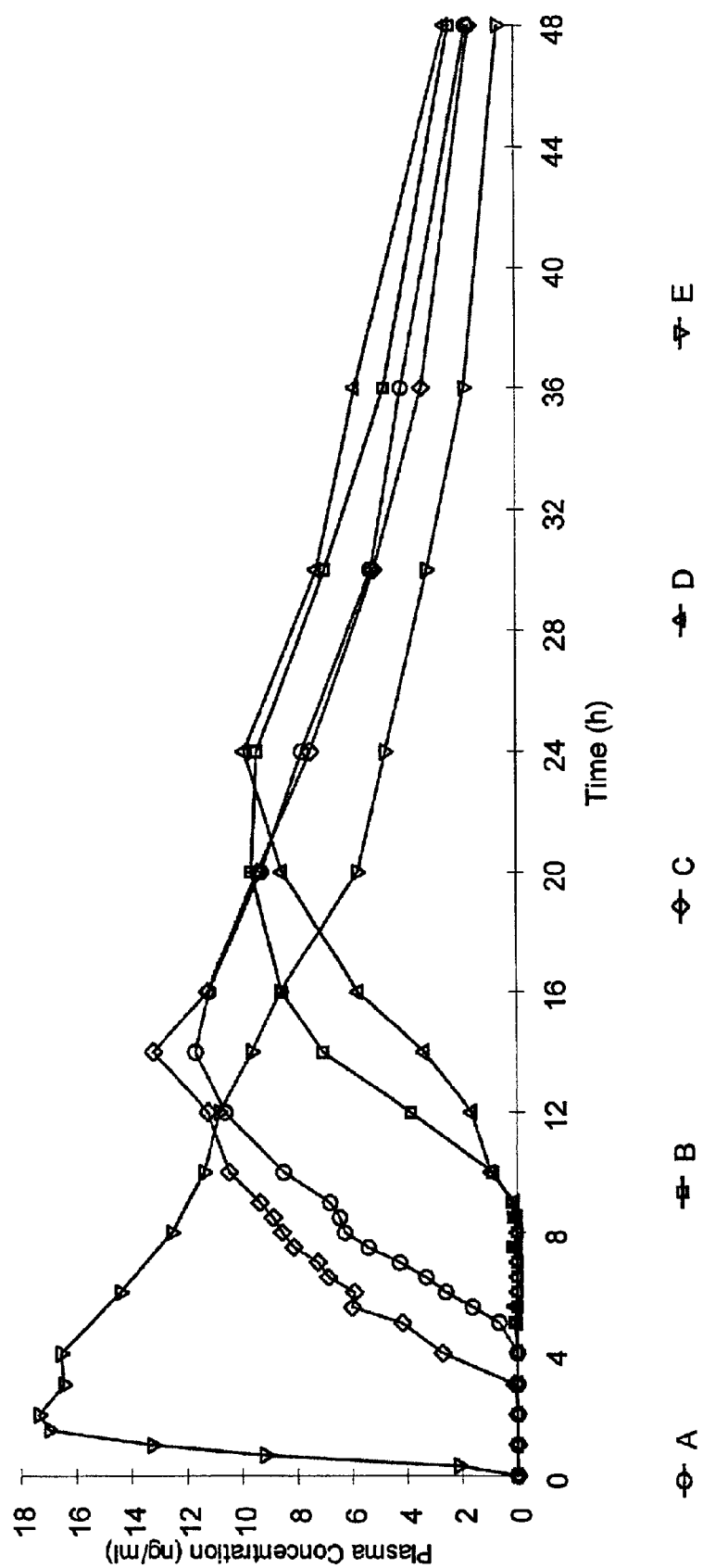
FIG. 3 is a graph of bisoprolol plasma concentration (ng/ml) versus time (hours) for the four products described in Example 14 and a reference.

Two volunteers dropped out of the study and samples from two other volunteers were lost leaving eleven evaluable/crossed-over subjects. The mean plasma concentrations for bisoprolol for these eleven volunteers are shown in FIG. 3. Labels A, B, C and D refer to the encapsulated formulations in Example 13 and E refers to the reference product. As shown in Table 5, all four formulations according to the invention achieved a tag compared to the reference product indicating that a formulated lag is required to develop a PM administered bisoprolol product.

TABLE 5

| PK Parameter | A | B | C | D | E |
| --- | --- | --- | --- | --- | --- |
| Cmax (ng/ml) | 12.697 ± 2.752 | 10.742 ± 2.076 | 13.704 ± 3.539 | 10.070 ± 2.961 | 19.479 ± 3.593 |
| AUC(0-∞) (ng/ml.h) | 305.931 ± 80.795 | 272.013 ± 58.673 | 317.212 ± 87.166 | 281.492 ± 81.862 | 317.796 ± 91.951 |
| Tmax (h) | 14.909 ± 2.071 | 20.727 ± 4.221 | 13.818 ± 1.662 | 22.182 ± 5.259 | 2.591 ± 1.530 |
| Tquant* (h) | 4–6 | 8–10 | 2–3 | 8–14 | |

*Tquant reported as a range is the time prior to the first quantifiable bisoprolol plasma concentration.

What is claimed is:

1. A multiparticulate bisoprolol formulation for once-daily oral administration, said formulation comprising at least two particles comprising a core of bisoprolol or a pharmaceutically acceptable salt thereof, and a polymeric coating comprising at least one polymer that exhibits a pH-dependent dissolution profile and imparts a pH-dependent delay in bisoprolol release, wherein following administration said formulation exhibits a lag in release, producing a bisoprolol plasma concentration of not more than about 1 ng/ml for at least about three hours, and thereafter provides a sustained release of bisoprolol that produces a therapeutic plasma concentration not later than about 12 hours following administration, and wherein said formulation maintains a therapeutic plasma concentration of bisoprolol for the remainder of a twenty-four hour period measured from administration.

2. The multiparticulate bisoprolol formulation according to claim 1, comprising a pharmaceutically acceptable salt of bisoprolol.

3. The multiparticulate bisoprolol formulation according to claim 2, wherein the bisoprolol salt is bisoprolol hemifumarate.

4. The multiparticulate bisoprolol formulation according to claim 1, which, when measured in a U.S. Pharmacopoeia 2 Apparatus (Paddles) in phosphate buffer at pH 6.8 at 37° C. and 50 rpm, exhibits a dissolution profile substantially corresponding to the following:
   (a) from 0% to 10% of the total bisoprolol is measured after 2 hours in said apparatus;
   (b) from 0% to 50% of the total bisoprolol is measured after 4 hours in said apparatus; and
   (c) greater than 50% of the total bisoprolol is measured after 10 hours in said apparatus.

5. The multiparticulate bisoprolol formulation according to claim 1, which, when measured in a U.S. Pharmacopoeia 1 Apparatus (Baskets) at 37° C. and 50 rpm in 0.01 N HCl for the first 2 hours followed by transfer to phosphate buffer at pH 6.8 for the remainder of the measuring period, exhibits a dissolution profile substantially corresponding to the following:
   (a) from 0% to 10% of the total bisoprolol is measured after 2 hours in said apparatus;
   (b) less than 50% of the total bisoprolol is measured after 4 hours in said apparatus; and
   (c) greater than 20% of the total bisoprolol is measured after 10 hours in said apparatus.

6. The multiparticulate bisoprolol formulation according to claim 1, wherein at least two particles comprise a sealant or barrier layer between the core and the polymeric coating.

7. The multiparticulate bisoprolol formulation according to claim 6, wherein the sealant or barrier layer comprises at least one of hydroxypropyl methylcellulose, hydroxypropyl cellulose, hydroxypropyl ethylcellulose or xanthan gum.

8. The multiparticulate bisoprolol formulation according to claim 1, wherein the polymeric coating comprises at least one pharmaceutically acceptable film-forming polymer that forms an insoluble film of low permeability and wherein said at least one polymer that forms an insoluble film of low permeability comprises from about 80 to about 100 percent of the polymers in said coating.

9. The multiparticulate bisoprolol formulation according to claim 8, wherein the polymeric coating comprises at least one pharmaceutically acceptable film-forming polymer that forms an insoluble film of high permeability comprises from about 0 to about 20 percent of the polymers in said coating.

10. The multiparticulate bisoprolol formulation according to claim 8, wherein the polymeric coating comprises a methacrylic acid co-polymer.

11. The multiparticulate bisoprolol formulation according to claim 8, wherein the polymeric coating comprises an ammonio methacrylate co-polymer.

12. The multiparticulate bisoprolol formulation according to claim 10, wherein the polymeric coating comprises a mixture of methacrylate co-polymers and ammonio methacrylate co-polymers.

13. The multiparticulate bisoprolol formulation according to claim 1, wherein the polymeric coating comprises at lest one soluble excipient.

14. The multiparticulate bisoprolol formulation according to claim 13, wherein the soluble excipient is chosen from soluble, polymers, surfactants, alkali metal salts, organic acids, sugars, and sugar alcohols.

15. The multiparticulate bisoprolol formulation according to claim 13, wherein the soluble excipient is chosen from polyvinyl pyrrolidone, polyethylene glycol, and mannitol.

16. The Multiparticulate bisoprolol formulation according to claim 13, wherein the soluble excipient is present in an amount of from 1% to 10% by weight, based on the total dry weight of polymer in the polymeric coating.

17. The multiparticulate bisoprolol formulation according to claim 1, wherein the polymeric coating comprises one or more auxiliary agents chosen from fillers, plasticizers, and anti-foaming agents.

18. The multiparticulate bisoprolol formulation according to claim 1, wherein the polymeric coating produce a weight gain of from about 10% to 100% to the core.

19. The multiparticulate bisoprolol formulation according to claim 18, wherein the polymeric coating produce a weight gain of from about 25% to 70% to the core.

20. The multiparticulate bisoprolol formulation according to claim 1, wherein a sealant or barrier is applied to the polymeric coating.

21. The multiparticulate bisoprolol formulation according to claim 20, wherein the sealant or barrier comprises at least one of hydroxypropyl methylcellulose, hydroxypropyl cellulose, hydroxypropyl ethylcellulose or xanthan gum.

22. An oral dosage form comprising a multiparticulate bisoprolol formulation according to claim 1, which is in the form of caplets, capsules, particles for suspension, sachets, or tablets.

23. The oral dosage form according to claim 22, which is in the form of tablets chosen from disintegrating tablets, fast dissolving tablets, effervescent tablets, fast melt tablets, and mini-tablets.

24. The multiparticulate bisoprolol formulation according to claim 9, wherein the polymeric coating comprises a methacrylic acid co-polymer.

25. The multiparticulate bisoprolol formulation according to claim 9, wherein the polymeric coating comprises an ammonio methacrylate co-polymer.

26. The multiparticulate bisoprolol formulation according to claim 9, wherein the polymeric coating comprises a mixture of methacrylate co-polymers and ammonio methacrylate co-polymers.

27. The multiparticulate bisoprolol formulation according to claim 1, wherein the polymeric coating comprises at least one polymer that dissolves in a pH-dependent manner.

28. The multiparticulate bisoprolol formulation according to claim 27, wherein the formulation releases bisoprolol in a manner that is dependent on the local pH of the gastrointestinal tract.

29. The multiparticulate bisoprolol formulation according to claim 1, wherein the polymeric coating comprises at least one polymer that dissolves in a pH-independent manner.

30. The multiparticulate bisoprolol formulation according to claim 29, wherein the formulation releases bisoprolol in a manner that is independent of the local pH of the gastrointestinal tract.

31. The multiparticulate bisoprolol formulation according to claim 1, wherein the formulation provides a sustained release of bisoprolol that produces a therapeutic plasma concentration not later than about 6 hours following administration.

32. The multiparticulate bisoprolol formulation according to claim 1, wherein the formulation further comprises talc.

33. The multiparticulate bisoprolol formulation according to claim 1, wherein the formulation comprises a substantially purified enantiomer of bisoprolol.

34. The multiparticulate bisoprolol formulation according to claim 33, wherein the substantially purified enantiomer of bisoprolol is (S)-bisoprolol.

35. The multiparticulate bisoprolol formulation according to claim 33, wherein the substantially purified enantiomer of bisoprolol is (R)-bisoprolol.

36. The multiparticulate bisoprolol formulation according to claim 1, wherein the polymeric coating comprises at least one pharmaceutically acceptable film-forming polymer that forms an insoluble film of low permeability.

37. The multiparticulate bisoprolol formulation according to claim 36, wherein the polymeric coating further comprises at least one pharmaceutically acceptable film-forming polymer that forms an insoluble film of high permeability.

38. The multiparticulate bisoprolol formulation according to claim 36, wherein at least one pharmaceutically acceptable film-forming polymer that forms an insoluble film of low permeability is present in an amount greater than the amount of any pharmaceutically acceptable film-forming polymers that form an insoluble film of high permeability.

\* \* \* \* \*